United States Patent
Fu et al.

(10) Patent No.: US 11,419,994 B2
(45) Date of Patent: Aug. 23, 2022

(54) VAPORIZATION DEVICE HAVING CHANNEL STRUCTURE

(71) Applicant: SHENZHEN RELX TECHNOLOGY CO., LTD., Shenzhen (CN)

(72) Inventors: Yao Fu, Shenzhen (CN); Zugang Yang, Shenzhen (CN); Shuting Feng, Shenzhen (CN); Jin Zhang, Shenzhen (CN)

(73) Assignee: SHENZHEN RELX TECHNOLOGY CO., LTD., Shenzhen (CN)

( * ) Notice: Subject to any disclaimer, the term of this patent is extended or adjusted under 35 U.S.C. 154(b) by 312 days.

(21) Appl. No.: 16/568,302

(22) Filed: Sep. 12, 2019

(65) Prior Publication Data

US 2021/0016021 A1    Jan. 21, 2021

(30) Foreign Application Priority Data

Jul. 16, 2019    (CN) .................. 201910642345.X (51) Int. Cl.
*A24F 13/00*    (2006.01)
*A24F 17/00*    (2006.01)
(Continued)

(52) U.S. Cl.
CPC ... *A61M 11/042* (2014.02); *A61M 2205/8206* (2013.01)

(58) Field of Classification Search
CPC ....... A24F 40/10; A24F 40/40; A61M 11/042; A61M 2205/8206
See application file for complete search history.

(56) References Cited

U.S. PATENT DOCUMENTS

2015/0272216 A1    10/2015    Dai et al.
2016/0219939 A1    8/2016    Li et al.
(Continued)

FOREIGN PATENT DOCUMENTS

CN    2719043 Y    8/2005
CN    106686997 A    5/2017
(Continued)

OTHER PUBLICATIONS

European Search Report of corresponding European Patent Application No. 19205413.8 dated Nov. 25, 2020.
(Continued)

*Primary Examiner* — Abdullah A Riyami
*Assistant Examiner* — Thang H Nguyen
(74) *Attorney, Agent, or Firm* — Idea Intellectual Limited; Margaret A. Burke; Sam T. Yip (57) ABSTRACT

The present application relates to a vaporization device. The vaporization device includes a housing, a heating component, a heating component cap, a heating component base, and a first sealing element disposed on the heating component cap. The housing and the first sealing element define a liquid storage compartment, and the heating component and the heating component base define an vaporization chamber. The heating component cap includes a first opening on a first surface, a second opening on a second surface, and a first channel passing through the first opening and the second opening. The first sealing element covers the first opening, and the second opening is in fluid communication with the vaporization chamber.

20 Claims, 7 Drawing Sheets

(51) Int. Cl.
　　　*A24F 25/00*　　　(2006.01)
　　　*A61M 11/04*　　　(2006.01)

(56) References Cited

U.S. PATENT DOCUMENTS

| | | | |
|---|---|---|---|
| 2018/0077968 A1* | 3/2018 | Qiu | A24F 40/46 |
| 2019/0022345 A1* | 1/2019 | Kotch | A61M 16/145 |
| 2019/0166907 A1 | 6/2019 | Chung | |
| 2020/0352238 A1* | 11/2020 | Simpson | A24F 40/485 |
| 2020/0367556 A1* | 11/2020 | Lin | A24F 40/46 |
| 2020/0397046 A1* | 12/2020 | Lin | A24F 40/30 |
| 2021/0059308 A1* | 3/2021 | Lin | A24F 40/40 |
| 2021/0127742 A1* | 5/2021 | Kim | A24F 40/42 |

FOREIGN PATENT DOCUMENTS

| | | | | |
|---|---|---|---|---|
| CN | 108135258 A | | 6/2018 | |
| CN | 108185536 A | | 6/2018 | |
| CN | 108308716 | * | 7/2018 | A24F 47/00 |
| CN | 108308716 A | | 7/2018 | |
| CN | 108685183 A | | 10/2018 | |
| CN | 108741232 A | | 11/2018 | |
| CN | 109007980 A | | 12/2018 | |
| CN | 109452691 A | | 3/2019 | |
| CN | 208550016 U | | 3/2019 | |
| KR | 20180124736 | * | 11/2018 | A24F 47/00 |

OTHER PUBLICATIONS

Evaluation Report of corresponding China Utility Model Patent Application No. 201921126995.0 completed on Sep. 7, 2020.
International Search Report and Written Opinion of corresponding PCT Patent Application No. PCT/CN2019/096146 dated Mar. 30, 2020.

* cited by examiner

VAPORIZATION DEVICE HAVING CHANNEL STRUCTURE

CROSS REFERENCE TO RELATED APPLICATIONS

The present application claims the benefit of priority from the China Patent Application No. 201910642345.X, filed on 16 Jul. 2019, the disclosure of which is hereby incorporated by reference in its entirety.

BACKGROUND OF THE INVENTION

1. Field of the Invention

The present application generally relates to a vaporization device, and more particularly to an electronic device for providing an inhalable aerosol.

2. Description of the Related Art

An electronic cigarette is an electronic product that heats and vaporizes a vaporizable solution to produce an aerosol for a user to inhale. In recent years, many manufacturers begin to produce various electronic cigarette products. Generally, an electronic cigarette product includes a housing, an e-liquid storage chamber, an vaporization chamber, a heating component, an air inlet, an airflow channel, an air outlet, a power supply device, a sensing device, and a control device. The e-liquid storage chamber is configured to store a vaporizable solution, and the heating component is configured to heat and vaporize the vaporizable solution to produce an aerosol. The air inlet is in communication with the vaporization chamber, and supplies air to the heating component when the user inhales. The aerosol generated by the heating component is first generated in the vaporization chamber, then flows through the airflow channel and the air outlet, and is finally inhaled by the user. The power supply device provides power required by the heating component, and the control device controls the heating time of the heating component based on the user's inhalation action detected by the sensing device. The housing wraps all the components described above.

Existing electronic cigarette products have different defects, which may be caused by improper design of relative positions between different components. For example, in a common electronic cigarette product, the heating component, the airflow channel, and the air outlet are designed to be aligned with each other in a vertical direction. Because the airflow channel has a certain length, the aerosol passing through the airflow channel may be cooled to form a condensate attached to the wall of the airflow channel. For this design, when the residual condensate reaches a particular volume, the condensate easily falls down from the airflow channel to contact with the heating component. The fallen condensate may contaminate the heating component and change the flavor of the aerosol. In addition, when the condensate directly falls onto the heating component with high temperature, the liquid may be splashed, and the splashed liquid may even burn the user.

In addition, the existing electronic cigarette products fail to take the pressure balance of the e-liquid storage chamber into consideration. In the existing electronic cigarette products, the e-liquid storage chamber is generally designed to be completely sealed to prevent spilling of the vaporizable solution. As the user continuously uses the electronic cigarette product, the amount of the vaporizable solution in the e-liquid storage chamber continuously decreases, so that the pressure in the e-liquid storage chamber decreases to form a negative pressure. The negative pressure makes it difficult for the vaporizable solution in the e-liquid storage chamber to evenly flow to the heating component, and the heating component cannot evenly absorb the vaporizable solution. In this case, when the temperature of the heating component rises, there will be a high probability that no vaporizable solution exists on part of the heating component during heating and a burning smell may be generated, resulting in poor user experience.

Therefore, a vaporization device which can resolve the above problem is provided.

SUMMARY OF THE INVENTION

A vaporization device is provided. The vaporization device includes a housing, a heating component, a heating component cap, a heating component base, and a first sealing element disposed on the heating component cap. The housing and the first sealing element define a liquid storage compartment, and the heating component and the heating component base define an vaporization chamber. The heating component cap includes a first opening on a first surface, a second opening on a second surface, and a first channel passing through the first opening and the second opening. The first sealing element covers the first opening, and the second opening is in fluid communication with the vaporization chamber.

A vaporization device is provided. The vaporization device includes a housing, a heating component cap, and a heating component base. The vaporization device further includes a first sealing element disposed on the heating component cap and a heating component disposed between the heating component cap and the heating component base. The heating component and the heating component base define an vaporization chamber. The heating component cap includes a first opening and a second opening on a first surface, where the first sealing element covers the first opening and exposes the second opening.

BRIEF DESCRIPTION OF THE DRAWINGS

The aspects of the present invention will become more comprehensible from the following detailed description made with reference to the accompanying drawings. It should be noted that, various features may not be drawn to scale, and the sizes of the various features may be increased or reduced arbitrarily for the purpose of clear description.

The drawings and detailed descriptions use the same reference numerals to indicate same or similar elements. The present invention will be more apparent from the detailed descriptions made with reference to the accompanying drawings.

PREFERRED EMBODIMENT OF THE PRESENT INVENTION

The following disclosed content provides many different embodiments or examples of different features used to implement the provided subject matters. The following describes particular examples of components and deployments. Certainly, there are merely examples and are not intended to be limitative. In the present invention, in the following descriptions, reference formed by the first feature above or on the second feature may include an embodiment formed by direct contact between the first feature and the second feature, and may further include an embodiment in which an additional feature may be formed between the first feature and the second feature to enable the first feature and the second feature to be not in direct contact. In addition, in the present invention, reference numerals and/or letters may be repeated in examples. This repetition is for the purpose of simplification and clarity, and does not indicate a relationship between the described various embodiments and/or configurations.

The embodiments of the present invention are described in detail below. However, it should be understood that, the present invention provides many applicable concepts that can be implemented in various particular cases. The described particular embodiments are only illustrative and do not limit the scope of the present invention.

Figure 1:
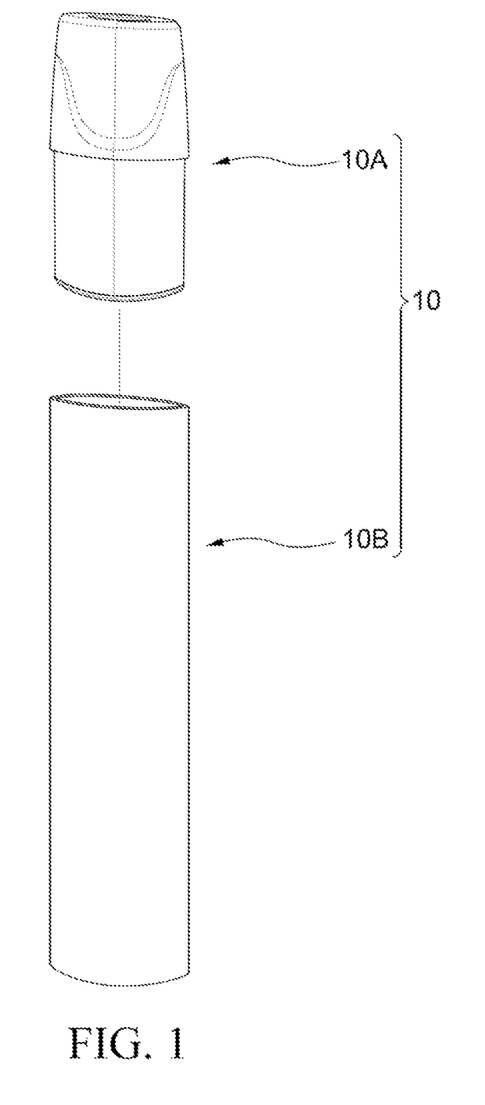
FIG. 1 is a schematic assembled view of a vaporization device according to some embodiments of the present disclosure.

FIG. 1 is a schematic assembled view of a vaporization device according to some embodiments of the present disclosure.

The vaporization device 10 may include a cartridge 10A and a body 10B. In some embodiments, the cartridge 10A and the body 10B may be designed as an integral device. In some embodiments, the cartridge 10A and the body 10B may be designed as two separate components. In some embodiments, the cartridge 10A may be designed to be removably combined with the body 10B. In some embodiments, the cartridge 10A may be designed to be partially received in the body 10B.

The body 10B may include many components therein. Although not shown in FIG. 1, the body 10B may include a conductive elastic pin, a sensor, a circuit board, a light guiding assembly, a buffer assembly, a power supply assembly (for example, but not limited to, a battery or a rechargeable battery), a power supply assembly bracket, a motor, a charging board, and other components required for operation of the vaporization device 10. The body 10B may provide a power supply to the cartridge 10A. The power supply provided by the body 10B to the cartridge 10A can heat a vaporizable material stored in the cartridge 10A. The vaporizable material may be a liquid. The vaporizable material may be a solution. In subsequent paragraphs of the present disclosure, the vaporizable material may also be referred to as an e-liquid. The e-liquid is edible.

Figure 2A:
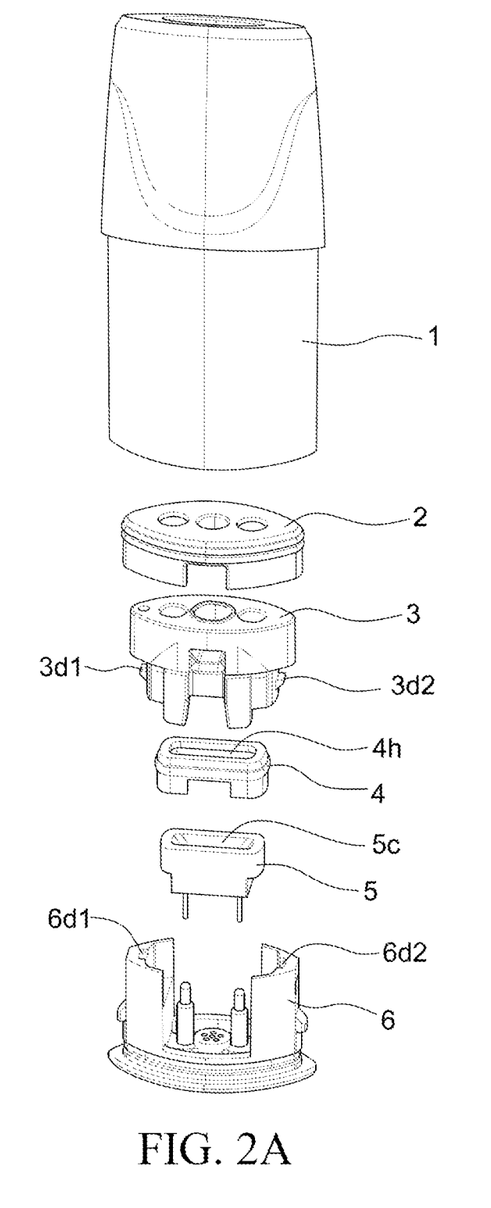
FIG. 2A and FIG. 2B are exploded views of part of a vaporization device according to some embodiments of the present disclosure.
Figure 2B:
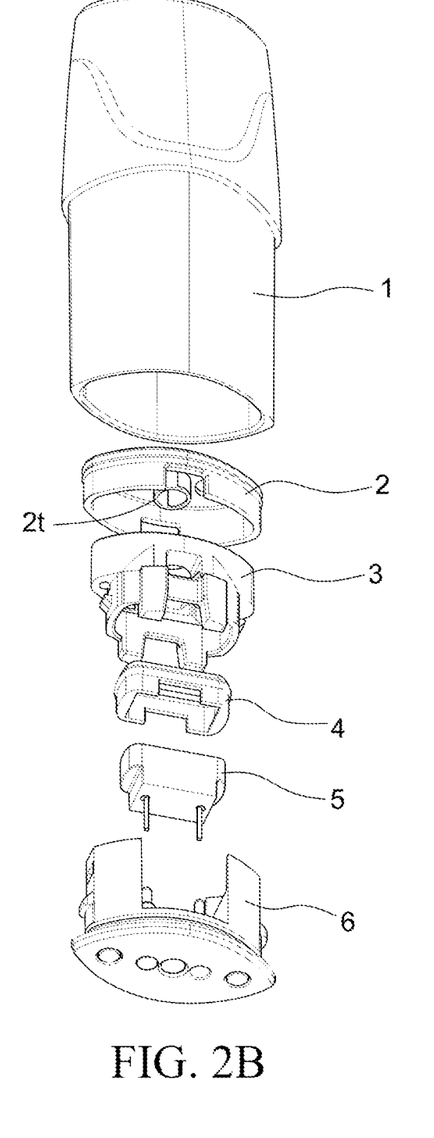

FIG. 2A and FIG. 2B are exploded views of a cartridge according to some embodiments of the present disclosure.

The cartridge 10A includes a housing 1, a cap sealing member 2, a heating component cap 3, a heating-assembly sealing member, a heating component 5, and a heating component base 6. The heating component 5 may have a heating circuit (not shown) on a surface thereof. The heating component 5 may have a heating circuit (not shown) therein.

As shown in FIG. 2A, the cap sealing member 2 may have a plurality of openings. The heating component cap 3 may have a plurality of openings. In some embodiments, the number of openings of the cap sealing member 2 and the number of openings of the heating component cap 3 may be the same. In some embodiments, the number of openings of the cap sealing member 2 and the number of openings of the heating component cap 3 may be different. In some embodiments, the number of openings of the cap sealing member 2 is less than the number of openings of the heating component cap 3. In some embodiments, the number of openings of the cap sealing member 2 is greater than the number of openings of the heating component cap 3.

In some embodiments, the cap sealing member 2 may be elastic. In some embodiments, the cap sealing member 2 may be flexible. In some embodiments, the cap sealing member 2 may include silica gel. In some embodiments, the cap sealing member 2 may be made of silica gel.

The heating component cap 3 may have buckle portions 3$d$1 and 3$d$2. The heating component base 6 may have buckle portions 3$d$1 and 3$d$2. The heating component cap 3 may be coupled to the heating component base 6 through the buckle portions 3$d$1, 3$d$2, 6$d$1 and 6$d$2. The heating component cap 3 may be mechanically combined with the heating component base 6 through the buckle portions 3$d$1, 3$d$2, 6$d$1 and 6$d$2. The heating component cap 3 may be removably combined with the heating component base 6 through the buckle portions 3$d$1, 3$d$2, 6$d$1 and 6$d$2.

When some or all of the components of the cartridge 10A are combined with each other, the upper sealing member 2 may cover a portion of the heating component cap 3. The cap sealing member 2 may surround a portion of the heating component cap 3. The cap sealing member 2 may expose a portion of the heating component cap 3.

When some or all of the components of the cartridge 10A are combined with each other, the heating-assembly sealing member may cover a portion of the heating component 5. The heating-assembly sealing member may surround a portion of the heating component 5. The heating-assembly sealing member may expose a portion of the heating component 5.

In some embodiments, the heating-assembly sealing member may be elastic. In some embodiments, the heating-assembly sealing member may be flexible. In some embodiments, the heating-assembly sealing member may include silica gel. In some embodiments, the heating-assembly sealing member may be made of silica gel.

As shown in FIG. 2A, the heating-assembly sealing member has an opening 4$h$, and the heating component 5 has a groove 5$c$. When the heating-assembly sealing member and the heating component 5 are combined with each other, the opening 4$h$ may expose at least a part of the groove 5$c$.

As is shown in FIG. 2B, the cap sealing member 2 may have an extending portion 2$t$. When the cap sealing member 2 and the heating component cap 3 is combined with each other, the extending portion 2$t$ extends into a channel of the heating component cap 3.

Figure 3A:
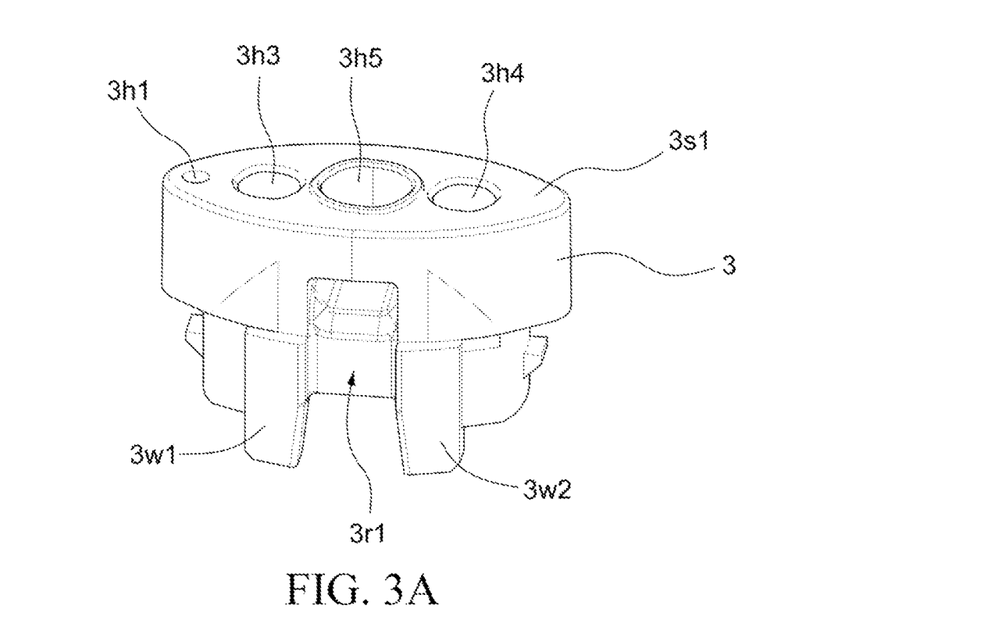
FIG. 3A and FIG. 3B are three-dimensional views of a heating component cap according to some embodiments of the present disclosure.
Figure 3B:
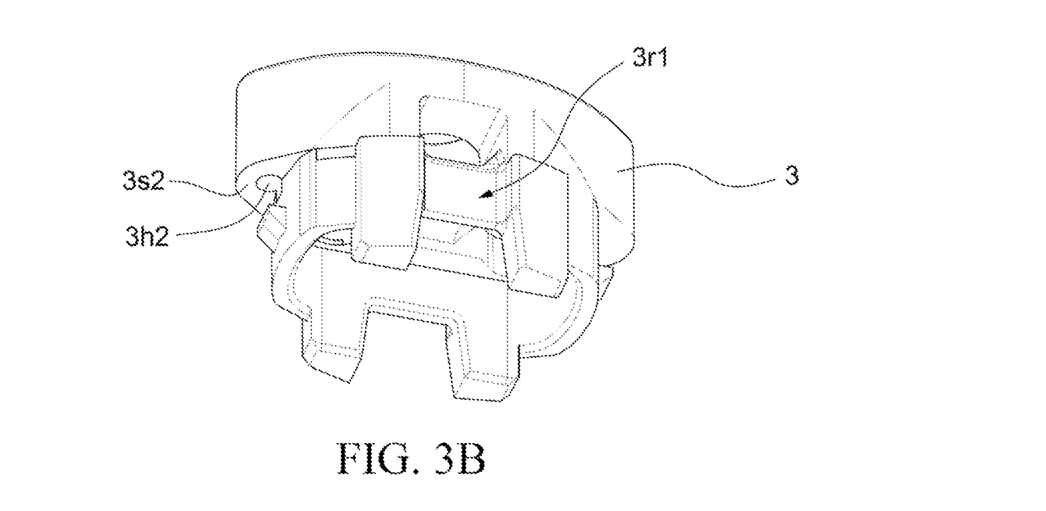

FIG. 3A and FIG. 3B are three-dimensional views of a heating component cap according to some embodiments of the present disclosure.

The heating component cap 3 has openings 3$h$1, 3$h$3, 3$h$4 and 3$h$5 on a surface 3$s$1. The opening 3$h$1 extends into the heating component cap 3 and forms a channel (for example, a channel 3$c$1 shown in FIG. 4A). The opening 3$h$3 extends into the heating component cap 3 and forms a channel (for example, a channel 3$c$2 shown in FIG. 4A). The opening 3$h$4 extends into the heating component cap 3 and forms a channel (for example, a channel 3c3 shown in FIG. 4A). The opening 3h5 extends into the heating component cap 3 and forms a channel (for example, a channel 3c4 shown in FIG. 4A). In some embodiments, the heating component cap 3 may have more channels. In some embodiments, the heating component cap 3 can have fewer channels.

The heating component cap 3 has pillar portions 3w1 and 3w2. The pillar portions 3w1 and 3w2 define a groove 3r1 therebetween. The groove 3r1 is in fluid communication with the opening 3h5. The groove 3r1 is in fluid communication with the channel 3c4 of the heating component cap 3 (shown in FIG. 4A). The groove 3r1 is in fluid communication with an vaporization chamber 6C (shown in FIG. 4A).

As shown in FIG. 3B, the heating component cap 3 has an opening 3h2 on a surface 3s2. The opening 3h1 runs through the heating component cap 3 from the surface 3s1 to the opening 3h2 on the surface 3s2 to form the channel 3c1. In some embodiments, the opening 3h1 and the opening 3h2 may be aligned with each other in a vertical direction. In some embodiments, the opening 3h1 and the opening 3h2 may be not aligned with each other in the vertical direction.

Figure 4A:
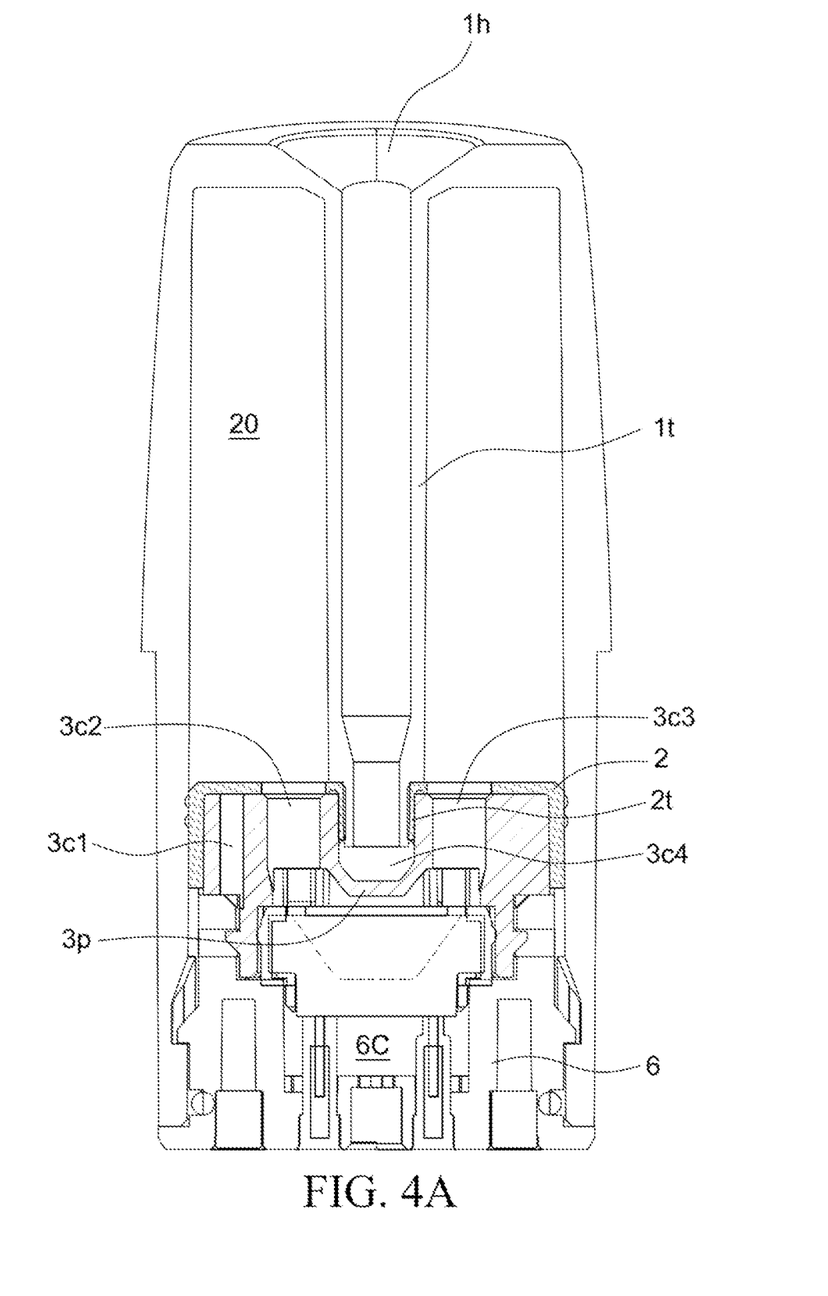
FIG. 4A and FIG. 4B are cross-sectional views of a cartridge according to some embodiments of the present disclosure.
Figure 4B:
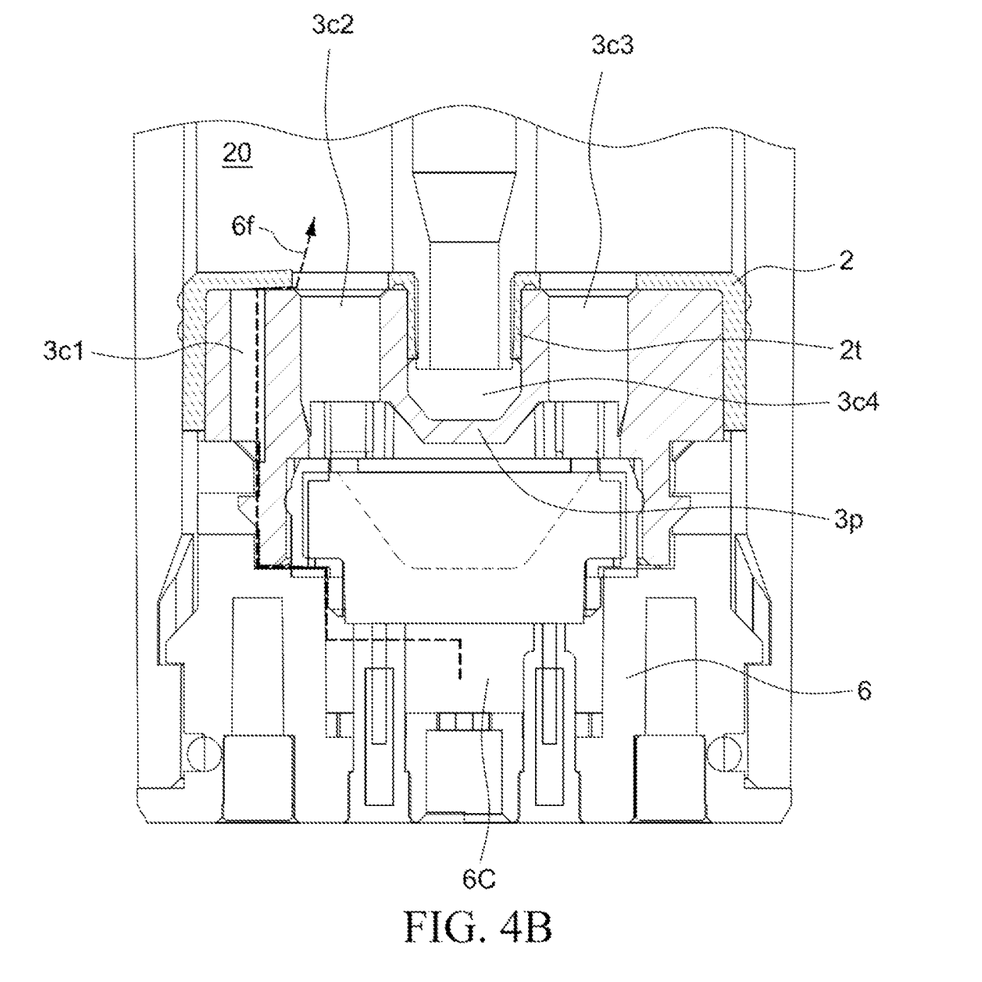

FIG. 4A and FIG. 4B are cross-sectional views of a cartridge according to some embodiments of the present disclosure.

As shown in FIG. 4A, the housing 1 has an opening 1h and a tube 1t extending from the opening 1h to the cap sealing member 2. The tube 1t, the cap sealing member 2, and the housing 1 define a liquid storage compartment 20. The vaporizable material may be stored in the liquid storage compartment 20.

The tube 1t may have a portion extending into the channel 3c4. The tube It may have an uneven outer diameter. As shown in FIG. 4A, the portion of the tube 1t extending into the channel 3c4 has a relatively small outer diameter. The tube 1t may have an uneven inner diameter. As shown in FIG. 4A, the portion of the tube 1t extending into the channel 3c4 has a relatively small inner diameter.

The tube 1t is coupled to the channel 3c4 through the opening 3h5 of the cap heating component 3. The tube 1t is in fluid communication with channel 3c4 through the opening 3h5 of the cap heating component 3. The channel 3c4 is isolated from the liquid storage compartment 20 through the tube 1t.

As shown in FIG. 4A, the cap sealing member 2 may expose the openings 3h3, 3h4 and 3h5 of the heating component cap 3. The cap sealing member 2 does not cover the openings 3h3, 3h4 and 3h5 of the heating component cap 3. The cap sealing member 2 does not block the channels 3c2, 3c3 and 3c4.

The channel 3c2 is in fluid communication with the groove 5c of the heating component 5. The channel 3c3 is in fluid communication with the groove 5c of the heating component 5. The e-liquid stored in the liquid storage compartment 20 may flow into the groove 5c through the channel 3c2. The e-liquid stored in the liquid storage compartment 20 may flow into the groove 5c through the channel 3c3. The groove 5c of the heating component 5 is in fluid communication with the liquid storage compartment 20. The e-liquid may be in full contact with the heating component 5 in the groove 5c. The heating circuit on the surface of or inside the heating component 5 may heat the e-liquid to generate an aerosol.

The heating component base 6 and the heating component 5 define the vaporization chamber 6C therebetween. The heating component 5 is partially exposed in the vaporization chamber 6C. The aerosol generated by the heating component 5 through heating is formed in the vaporization chamber 6C. The aerosol generated by the heating component 5 through heating flows through the tube 1t and the opening 1h and is then inhaled by the user. The tube 1t is in fluid communication with the vaporization chamber 6C. The groove 3r1 is in fluid communication with the vaporization chamber 6C.

The cap sealing member 2 may cover the opening 3h1 of the heating component cap 3. The cap sealing member 2 may block the channel 3c1.

As shown in FIG. 4A, the heating component cap 3 has a blocking element 3p. The blocking element 3p isolates the tube 1t from the groove 5c of the heating component 5. The blocking element 3p isolates the channel 3c4 from the groove 5c of the heating component 5.

During the process of using the vaporization device, when the residual condensate in the tube 1t reaches a particular volume, the condensate may fall from the tube 1t. The blocking element 3p can prevent the condensate falling from the tube 1t from coming into contact with the heating component 5. The blocking element 3p can prevent the fallen condensate from contaminating the heating component 5. The blocking element 3p can prevent the fallen condensate from changing the flavor of the aerosol. The blocking element 3p can prevent the condensate from falling onto the heating component with high temperature to cause splashing of the liquid. The blocking element 3p can prevent the splashed liquid from burning the user.

FIG. 4B shows an airflow 6f from the vaporization chamber 6C to the liquid storage compartment 20.

When the vaporization device is placed still and not used by the user, the opening 3h1 is tightly combined with the cap sealing member 2, and the e-liquid in the liquid storage compartment 20 does not leak out from the channel 3c1.

As the user continuously uses the vaporization device, the amount of the vaporizable solution in the liquid storage compartment 20 continuously decreases, so that the pressure in the liquid storage compartment 20 gradually decreases. The decrease in the pressure in the liquid storage compartment 20 may lead to the formation of a negative pressure. The decrease in the pressure in the liquid storage compartment 20 makes it difficult for the vaporizable solution to flow to the groove 5c of the heating component 5 through the channels 3c2 and 3c3. When the groove 5c does not completely absorb the vaporizable solution, no vaporizable solution exists on part of the heating component during heating and a burning smell may be generated.

The foregoing problem can be resolved by including the channel 3c1 in the heating component cap 3. The channel 3c1 disposed within the heating component cap 3 can balance the pressure in the liquid storage compartment 20. Because the vaporization chamber 6C is in fluid communication with the tube 1t, the pressure in the vaporization chamber 6C is approximately equal to one atmospheric pressure. As the vaporizable solution in the liquid storage compartment 20 continuously decreases, the pressure in the liquid storage compartment 20 gradually decreases to less than one atmospheric pressure. The pressure difference between the vaporization chamber 6C and the liquid storage compartment 20 causes the airflow 6f from the vaporization chamber 6C to reach a junction between the opening 3h1 and the cap sealing member 2 through the channel 3c1. The airflow 6f may partially push away the cap sealing member 2. The airflow 6f may partially deform the cap sealing member 2. The airflow 6f may enter the liquid storage compartment 20 through a gap generated by the deformation of the cap sealing member 2. The airflow 6f entering the liquid storage compartment 20 can increase the pressure in the liquid storage compartment 20. The airflow 6f entering the liquid storage compartment 20 can balance the pressure between the liquid storage compartment 20 and the vaporization chamber 6C.

In some embodiments, the heating component cap 3 may be additionally provided with a channel which has the same function as the channel 3c1. For example, the heating component cap 3 may also be provided with a ventilation channel close to the opening 3h4.

Figure 5:
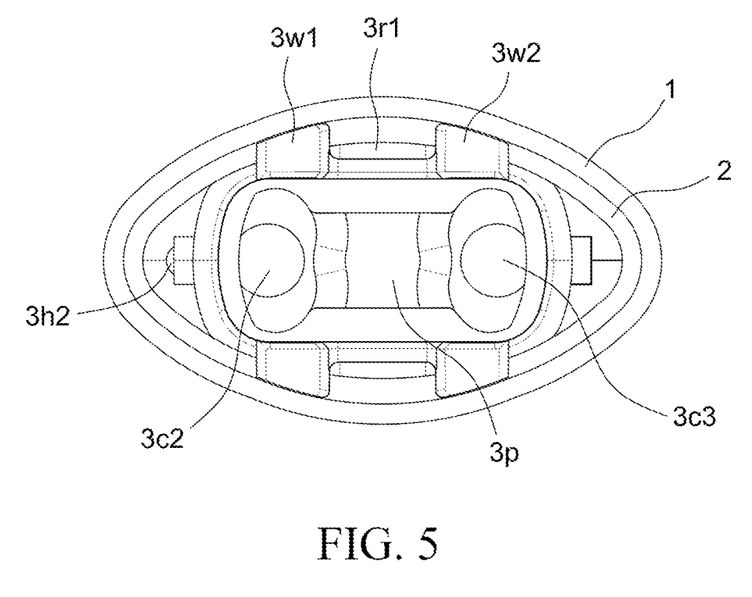
FIG. 5 is a bottom view of part of a cartridge according to some embodiments of the present disclosure.

FIG. 5 is a bottom view of part of a cartridge according to some embodiments of the present disclosure.

FIG. 5 is a bottom view showing that the housing 1, the cap sealing member 2 and the heating component cap 3 are combined with each other. The cap sealing member 2 is disposed between the housing 1 and the heating component cap 3.

The groove 3r1 is formed between the pillar portions 3w1 and 3w2. The groove 30 is formed between the heating component cap 3 and the housing 1. The groove 30 creates a space between the heating component cap 3 and the housing 1. The groove 30 enables the channel 3c4 of the heating component cap 3 to be in fluid communication with the vaporization chamber 6C. The blocking element 3p is disposed between the channels 3c2 and 3c3. The blocking element 3p may prevent the condensate falling from the tube 1t from coming into contact with the heating component 5.

As used herein, space-related terms such as "under", "below", "lower portion", "above", "upper portion", "lower portion", "left side", "right side", and the like may be used herein to simply describe a relationship between one element or feature and another element or feature as shown in the figures. In addition to orientation shown in the figures, space-related terms are intended to encompass different orientations of the device in use or operation. An apparatus may be oriented in other ways (rotated 90 degrees or at other orientations), and the space-related descriptors used herein may also be used for explanation accordingly. It should be understood that when a component is "connected" or "coupled" to another component, the component may be directly connected to coupled to another component, or an intermediate component may exist.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all ranges disclosed herein include endpoints. The term "substantially coplanar" may refer to two surfaces within a few micrometers (μm) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, if a difference between two values is less than or equal to ±10% of an average value of the value (for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%), it could be considered that the two values are "substantially" the same. For example, being "substantially" parallel may refer to an angular variation range of less than or equal to ±10° with respect to 0°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, being "substantially" perpendicular may refer to an angular variation range of less than or equal to ±10° with respect to 90°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

For example, two surfaces can be deemed to be coplanar or substantially coplanar if a displacement between the two surfaces is no greater than 5 μm, no greater than 2 μm, no greater than 1 μm, or no greater than 0.5 μm. A surface can be deemed to be planar or substantially planar if a difference between any two points on the surface is no greater than 5 μm, no greater than 2 μm, no greater than 1 μm, or no greater than 0.5 μm.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

As used herein, the singular terms "a," "an," and "the" may include plural referents unless the context clearly dictates otherwise. In the description of some embodiments, assemblies provided "on" or "above" another assembly may encompass a case in which a former assembly is directly on a latter assembly (for example, in physical contact with the latter assembly), and a case in which one or more intermediate assemblies are located between the former assembly and the latter assembly.

Unless otherwise specified, space descriptions such as "above", "below", "up", "left", "right", "down", "top portion", "bottom portion", "vertical", "horizontal", "side face", "higher than", "lower than", "upper portion", "on", "under", "downward", etc. are indicated relative to the orientation shown in the figures. It should be understood that the space descriptions used herein are merely for illustrative purposes, and actual implementations of the structures described herein may be spatially arranged in any orientation or manner, provided that the advantages of embodiments of the present invention are not deviated due to such arrangement.

While the present invention has been described and illustrated with reference to specific embodiments thereof, these descriptions and illustrations do not limit the present invention. It should be understood by those skilled in the art that various changes may be made and equivalents may be substituted without departing from the true spirit and scope of the present invention as defined by the appended claims. The illustrations may not be necessarily drawn to scale. There may be distinctions between the artistic renditions in the present invention and the actual apparatus due to manufacturing processes and tolerances. There may be other embodiments of the present invention which are not specifically illustrated. The specification and drawings are to be regarded as illustrative rather than restrictive. Modifications may be made to adapt a particular situation, material, composition of matter, method, or process to the objective, spirit and scope of the present invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present invention. Therefore, unless otherwise specifically indicated herein, the order and grouping of operations shall not be construed as any limitation on the present application.

Several embodiments of the present invention and features of details are briefly described above. The embodiments described in the present invention may be easily used as a basis for designing or modifying other processes and structures for realizing the same or similar objectives and/or obtaining the same or similar advantages introduced in the embodiments of the present invention. Such equivalent construction does not depart from the spirit and scope of the present invention, and various variations, replacements, and modifications can be made without departing from the spirit and scope of the present invention.

What is claimed is:

1. A vaporization device, comprising:
   a housing, a heating component, a heating component cap, a heating component base, and a first sealing element disposed on the heating component cap, wherein
   the housing and the first sealing element define a liquid storage compartment, and the heating component and the heating component base define an vaporization chamber;
   the heating component cap comprises a first opening on a first surface, a second opening on a second surface, and a first channel passing through the first opening and the second opening; and
   the first sealing element covers the first opening, and the second opening is in fluid communication with the vaporization chamber.

2. The vaporization device according to claim 1, wherein the heating component cap further comprises a second channel, the second channel forms a third opening on the first surface of the heating component cap, and the first sealing element exposes the third opening.

3. The vaporization device according to claim 1, wherein the heating component cap further comprises a third channel, the third channel forms a fourth opening on the first surface of the heating component cap, and the first sealing element exposes the fourth opening.

4. The vaporization device according to claim 2, wherein the heating component comprises a groove, the second channel is in fluid communication with the groove of the heating component, and the second channel is in fluid communication with the liquid storage compartment.

5. The vaporization device according to claim 3, wherein the heating component comprises a groove, the third channel is in fluid communication with the groove of the heating component, and the third channel is in fluid communication with the liquid storage compartment.

6. The vaporization device according to claim 1, wherein the heating component cap further comprises a fourth channel, the fourth channel forms a fifth opening on the first surface of the heating component cap, the first sealing element exposes the fifth opening, and the fourth channel is in fluid communication with the vaporization chamber.

7. The vaporization device according to claim 6, wherein the housing comprises a first tube extending into the liquid storage compartment, the first tube is coupled to the fourth channel through the fifth opening, and the fourth channel is isolated from the liquid storage compartment by the first tube.

8. The vaporization device according to claim 7, wherein the first tube comprises a first portion and a second portion, an outer diameter of the second portion is less than an outer diameter of the first portion, and the second portion extends into the fourth channel.

9. The vaporization device according to claim 1, wherein the heating component cap further comprises a fourth channel and the heating component comprises a groove, wherein the fourth channel is isolated from the groove.

10. A vaporization device, comprising:
    a housing, a heating component cap, a heating component base, a first sealing element disposed on the heating component cap, and a heating component disposed between the heating component cap and the heating component base, wherein
    the heating component and the heating component base define an vaporization chamber; and
    the heating component cap comprises a first opening and a second opening on a first surface, wherein the first sealing element covers the first opening and exposes the second opening.

11. The vaporization device according to claim 10, wherein the heating component base comprises a first buckle portion and a second buckle portion, and the heating component base is removably combined with the heating component cap through the first buckle portion and the second buckle portion.

12. The vaporization device according to claim 10, wherein the heating component cap further comprises a third opening on a second surface and a first channel extending from the first opening to the third opening, and the third opening is in fluid communication with the vaporization chamber.

13. The vaporization device according to claim 10, wherein the housing and the first sealing element define a liquid storage compartment, and the heating component comprises a first portion in fluid communication with the liquid storage compartment and a second portion exposed to the vaporization chamber.

14. The vaporization device according to claim 10, wherein the housing and the first sealing element define a liquid storage compartment, the second opening extends into the heating component cap to form a second channel, and the heating component is in fluid communication with the liquid storage compartment through the second channel.

15. The vaporization device according to claim 10, further comprising a second sealing element disposed between the heating component and the heating component cap, wherein the second sealing element surrounds the heating component and exposes at least a portion of the heating component.

16. The vaporization device according to claim 10, wherein the heating component cap further comprises a third channel, the third channel forms a fourth opening on the first surface of the heating component cap, the first sealing element exposes the fourth opening, and the third channel is in fluid communication with the vaporization chamber.

17. The vaporization device according to claim 16, wherein the housing and the first sealing element define a liquid storage compartment, the housing comprises a first tube extending into the liquid storage compartment, the first tube is coupled to the third channel through the fourth opening, and the third channel is isolated from the liquid storage compartment by the first tube.

18. The vaporization device according to claim 16, wherein the first sealing element comprises a portion extending into the third channel.

19. The vaporization device according to claim 10, wherein the first opening is smaller than the second opening.

20. The vaporization device according to claim 10, wherein the heating component cap further comprises a third channel and the heating component comprises a groove, wherein the third channel is isolated from the groove.

* * * * *